US00PP34604P2

(12) United States Plant Patent
Smit

(10) Patent No.: US PP34,604 P2
(45) Date of Patent: Sep. 20, 2022

(54) ***PEPEROMIA* PLANT NAMED 'EC-PEPE-2104'**

(50) Latin Name: *Peperomia obtusifolia*
Varietal Denomination: EC-PEPE-2104

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/677,619

(22) Filed: Feb. 22, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373, 263.1
CPC ... A01H 5/12; A01H 5/00; A01H 5/02; A01H 6/00
See application file for complete search history.

(56) References Cited

U.S. PATENT DOCUMENTS

PP29,598 P3 * 8/2018 Smit ..... A01H 6/00
Plt./373

OTHER PUBLICATIONS

CPVO Register 4.1.45 for *Peperomia* EC PEPE 2104, retrieved on Mar. 28, 2022 at https://online.plantvarieties.eu/public-ConsultationDetails?registerId=20211457&denomination=ec%20pepe%202104, 3 pp. (Year: 2022).*
Gould et al. Why some stems are red; cauline anthocyanins shield photosystem II against high light stress. Journal of Experimental Botany, vol. 6, No. 10, pp. 2707-2717, 2010. (Year: 2010).*

* cited by examiner

*Primary Examiner* — June Hwu
(74) *Attorney, Agent, or Firm* — Cassandra Bright

(57) ABSTRACT

A new and distinct cultivar of *Peperomia* plant named 'EC-PEPE-2104' is disclosed, characterized by red-brown stems, and glossy-green leaves. Plants have a compact, upright habit, and good branching. The new variety is a *Peperomia*, typically used as an ornamental plant.

3 Drawing Sheets

Latin name of the genus and species: *Peperomia obtusifolia.*

Variety denomination: 'EC-PEPE-2104'.

BACKGROUND OF THE INVENTION

The new cultivar is a product of a planned breeding program to produce distinct and better performing *Peperomia* varieties. The new variety was selected as a seedling resulting from the crossing of *Peperomia obtusifolia* '#1402', and '#1405', two unpatented varieties from the inventor's breeding line. The crossing was made by the inventor, Obed J. Smit, a citizen of the Netherlands in 2016. 'EC-PEPE-2104' was selected by the inventor in 2017 at a commercial greenhouse in Sappemeer, the Netherlands.

Asexual reproduction of the new cultivar 'EC-PEPE-2104' by terminal cuttings was first performed in Sappemeer, the Netherlands at a commercial greenhouse in September 2017, and has shown that the unique features of this cultivar are stable and reproduced true to type through successive generations.

SUMMARY OF THE INVENTION

The cultivar 'EC-PEPE-2104' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2104'. These characteristics in combination distinguish 'EC-PEPE-2104' as a new and distinct *Peperomia* cultivar:

1. Glossy green leaves.
2. Red-brown stems with short internodes.
3. Compact, upright-growing plant habit.
4. Good branching, new side-shoots develop naturally from the axils.

PARENT COMPARISON

Plants of the new cultivar 'EC-PEPE-2104' are similar to plants of the female parent, *Peperomia obtusifolia* '#1402' in most horticultural characteristics, however, plants of the new cultivar 'EC-PEPE-2104' differ from in the following characteristics:

1. Stems of the new variety are red-brown colored, while stems of the seed parent are brown.
2. Stems of the new variety are thicker than stems of the seed parent.
3. Leaves of the new variety are glossy-green, while leaves of the seed parent are light-green.
4. Leaves of the new variety are smaller than leaves of the seed parent.

Plants of the new cultivar 'EC-PEPE-2104' are similar to plants of the male parent, *Peperomia obtusifolia* '#1405' in most horticultural characteristics, however, plants of the new cultivar 'EC-PEPE-2104' differ in the following characteristics:

1. Stems of the new variety are thinner than stems of the pollen parent.
2. Leaves of the new variety are glossy-green, while leaves of the pollen parent are dark-green.

COMMERCIAL COMPARISON

Plants of the new cultivar 'EC-PEPE-2104' are similar to plants of the commercial variety *Peperomia obtusifolia* 'EC-PEPE-1806', U.S. Plant Pat. No. 31,313. However, plants of the new cultivar differ in the following characteristics:

1. Stems of the new variety are red-brown colored, while stems of this comparator are red.
2. Leaves of the new variety are glossy-green colored, while leaves of this comparator are light-green.
3. Leaves of the new variety are smooth with veins that are hardly visible; leaves of this comparator have more visible, deep-lying veins.

Plants of the new cultivar 'EC-PEPE-2104' are similar to plants of *Peperomia obtusifolia* 'Obtipan', U.S. Plant Pat. No. 29,598. However, plants of the new cultivar differ in the following characteristics:

1. Stems of the new variety are red-brown colored, while stems of this comparator are brown when immature and green when mature.
2. Leaves of the new variety are glossy-green, while leaves of this comparator are dark-green.

BRIEF DESCRIPTION OF THE PHOTOGRAPHS

The accompanying photograph in FIG. 1 illustrates in full color a typical blooming plant of 'EC-PEPE-2104' grown in a greenhouse. The plant is approximately 7 months of age.

Figure 1:
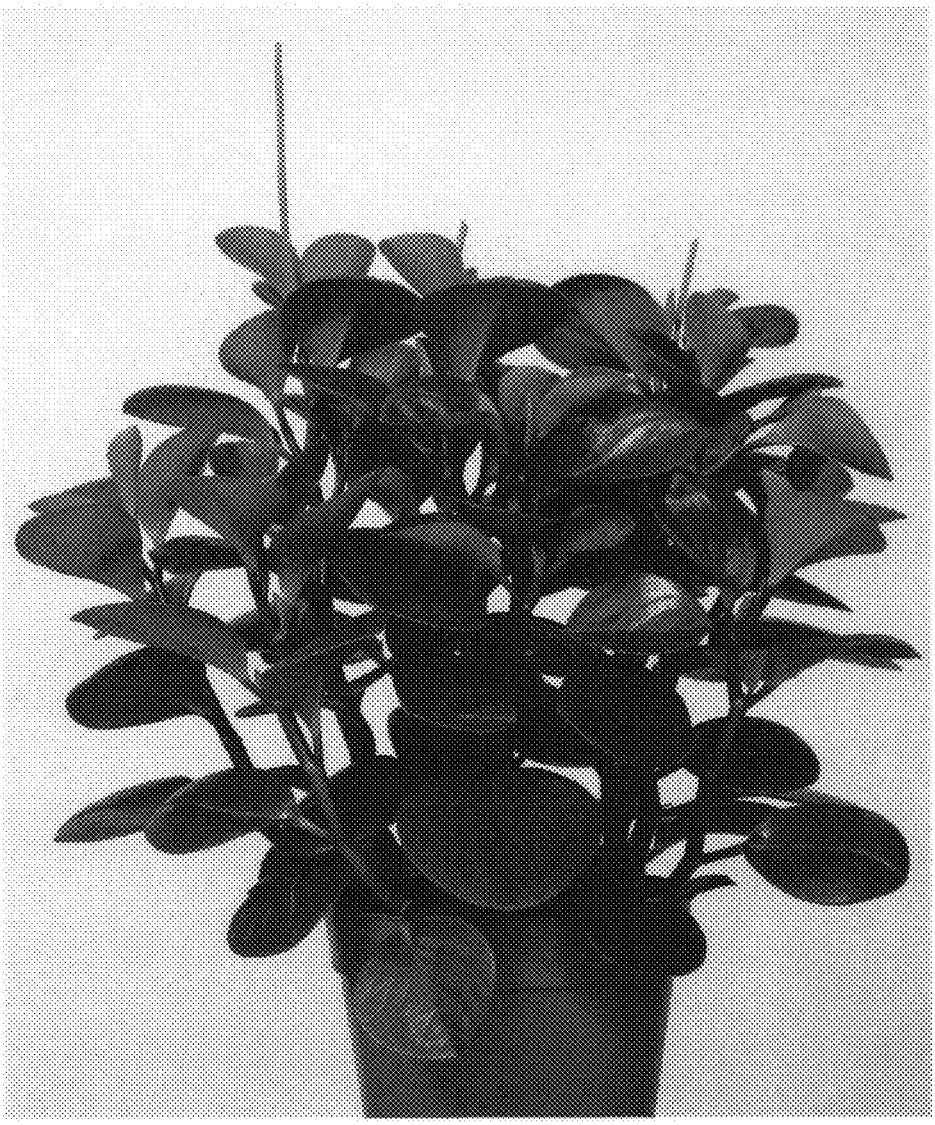
Figure 2:
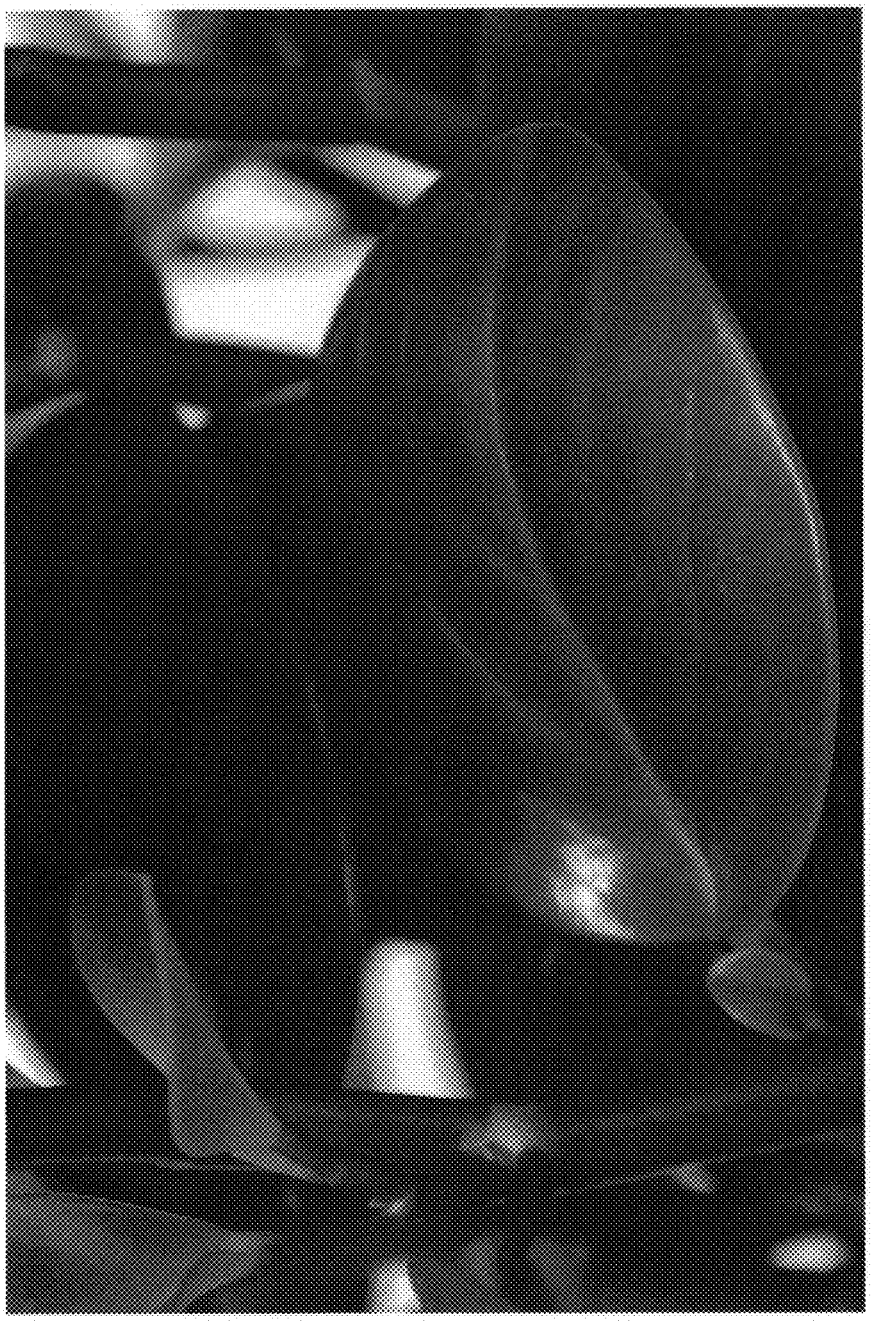
FIG. 2 illustrates a close up of the foliage.
Figure 3:
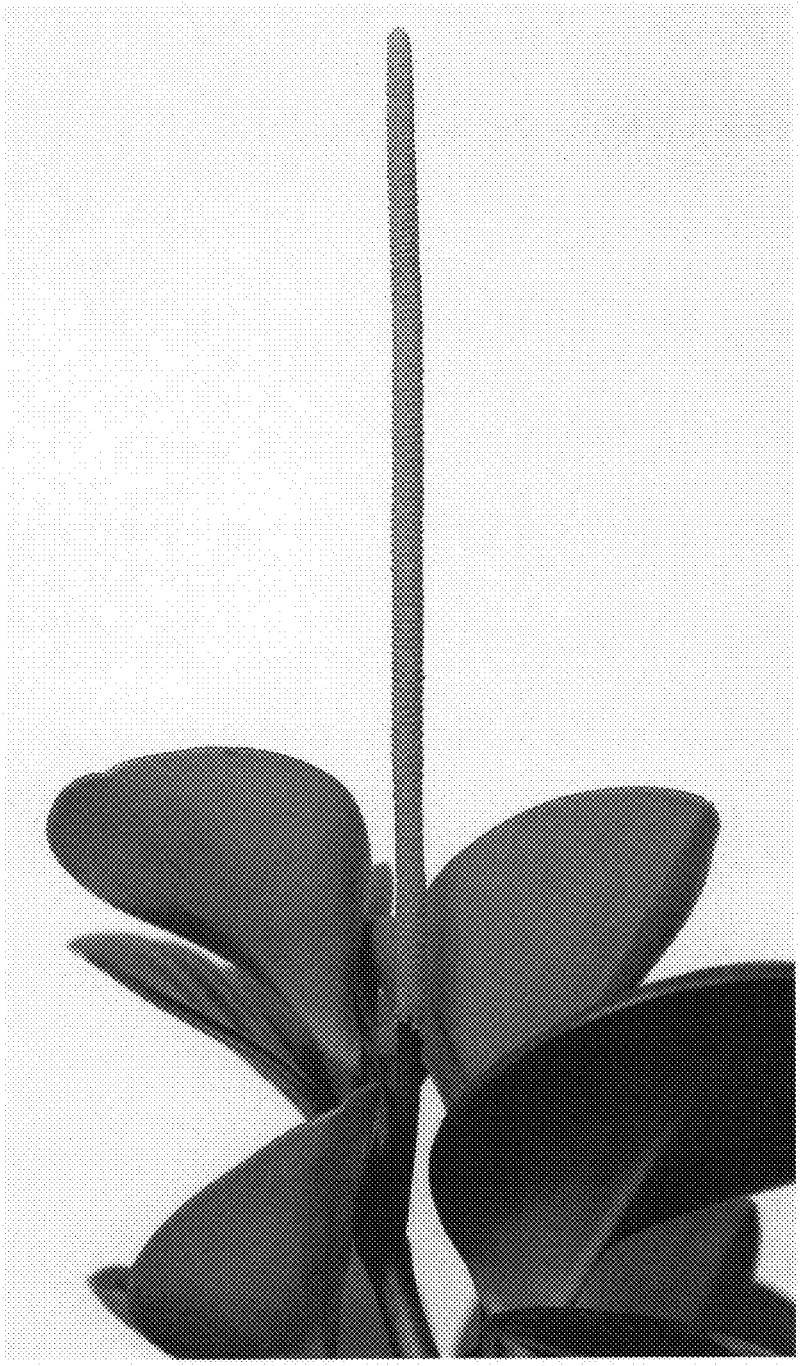
FIG. 3 illustrates typical inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2104' plants at 7 months of age, grown in a greenhouse in Sappemeer, the Netherlands during October. The growing temperature ranged from 18° C. to 20° C. at night to 20° C. to 23° C. during the day. Measurements and numerical values represent averages of typical flowering types.

Botanical classification: *Peperomia obtusifolia* 'EC-PEPE-2104'.

PROPAGATION

Time to initiate roots: About 7 days at approximately 20° C. in summer.

Time to produce rooted cutting: About 10 days at 20° C. in summer.

Description of roots: Fibrous, fine, moderately dense, freely branching. White in color, not accurately measured with R.H.S. chart.

PLANT

Plant type: Perennial potted plant.

Plant shape: Obovate.

Growth habit: Basal and lateral branching.

Plant spread: Approximately 23.3 cm.

Height: 29.2 cm to top of foliar plane; 36.1 cm to top of floral plane.

Growth rate: Moderate.

Plant vigor: Moderate to high.

Age of plant described: Approximately 7 months.

Branching habit: Basal and lateral branching.

Pinching: Pinching not required.

Number of primary (main) branches per plant: Average 3.

Number of secondary (lateral) branches per plant: Average 7.

Main branches:

*Length*.—Average: 9.5 cm.

*Diameter*.—Average: 0.6 cm.

Internode length: Average: 3.4 cm.

Appearance and shape: Succulent, thick and rounded.

Luster: Glossy.

Aspect/angle from vertical: Average angle: 40°.

Strength: Moderately strong.

Color:

*Developing*.—RHS Greyed-Orange 176A.

*Mature*.—Base color near Yellow-Green 146D, nearly completely covered in a strong anthocyanin layer near Greyed-Orange 176A. Base color 146D only showing as irregular stripes and flushes.

*At internodes*.—RHS Yellow-Green 147C, finely, irregularly striped and flushed Greyed-Orange 176B.

*Older stems*.—RHS Yellow-Green N148A and N148B, slightly finely, irregularly striped and flushed with an anthocyanin layer Greyed-Red 182B.

Pubescence: None.

FOLIAGE

Leaf:

*Arrangement*.—Alternate, single.

*Quantity*.—Average 7 per lateral branch.

*Average length*.—7.6 cm.

*Average width*.—6.9 cm.

*Shape of blade*.—Broad ovate to near orbicular.

*Aspect*.—Slightly convex.

*Apex*.—Obtuse to retuse.

*Base*.—Short attenuate.

*Margin*.—Entire.

*Texture of top surface*.—Glabrous, smooth, leathery.

*Texture of bottom surface*.—Glabrous, smooth, leathery.

*Pubescence*.—None.

*Luster, upper side*.—Glossy.

*Luster, under side*.—Moderately glossy.

*Color*.—Young foliage upper side: RHS Yellow-Green 144A. Young foliage under side: RHS Yellow-Green 144B. Mature foliage upper side: RHS Green NN137A. Mature foliage under side: RHS Yellow-Green 144A.

*Venation*.—Pattern: Pinnate. Venation color upper side: RHS Yellow-Green 145A. Venation color under side: RHS Yellow-Green 147D.

*Petiole*.—Average Length: 1.5 cm. Diameter: Petiole flattened, average diameter at widest (horizontally) 0.4 cm; at narrowest (vertically) 0.3 cm. Texture: Glabrous, smooth. Luster: Both sides moderately glossy. Strength: Medium. Color, upper side: Anthocyanin layer colored near RHS Greyed-Purple 183B cover a base layer of Yellow-Green 145A. Base layer visible as fine, irregular stripes. Color, under side: Anthocyanin layer colored near RHS Greyed-Purple 183A, over a base layer near Yellow-Green 147D. Base layer only appears as fine, irregular flushing.

FLOWER

Inflorescence:

*Arrangement*.—Axillary spike.

*Type and form*.—Spike.

*Height*.—Average 7.9 to 14.4 cm, excluding peduncle.

*Diameter*.—Average 0.3 cm.

*Flowers per inflorescence*.—Approximately 2,500 individual flowers per spike.

*Flowers and buds per plant*.—Approximately 12,500.

Bud:

*Length*.—Approximately 0.3 mm.

*Diameter*.—Approximately 0.3 mm.

*Shape*.—Flattened, orbicular.

*Texture*.—Glabrous, smooth, moderately velvety.

*Luster*.—Slightly glossy.

*Color*.—Near RHS Yellow-Green 146D.

Flower:

*Type and form*.—Individual flowers are very small and consist of 1 bract, 2 stamens, and a single pistil.

*Aspect*.—Outward.

*Habit*.—Very freely flowering.

*Fragrance*.—None.

*Shape*.—Rotate, consisting of 1 bract, 2 stamens, and 1 pistil; no petals or sepals present.

*Height*.—Average 1 mm.

*Diameter*.—Average 0.5 mm.

*Length*.—Average 0.4 mm.

*Longevity on plant*.—Average 1 month.

*Persistent or self-cleaning*?.—Self-cleaning.

Peduncles:

*Terminal length*.—Average 3.2 to 4.3 cm.

*Terminal diameter*.—Average 3 mm.

*Angle*.—Average 15° to lateral branch axis.

*Strength*.—Weak.

*Texture*.—Glabrous, smooth.

*Luster*.—Slightly glossy.

*Color*.—RHS Greyed-Green 196B, slightly to moderately finely striped Greyed-Red 182B.

Bracts:

*Length*.—Average 0.5 mm.

*Width*.—Average 0.4 mm.

*Shape*.—Orbicular.

*Color*.—Near RHS Green 143C.

REPRODUCTIVE ORGANS

Stamens:

*Number per flower*.—Average 2.

*Filament length*.—0.1 mm or shorter.

*Filament color*.—Near RHS Yellow-Green Group, impossible to measure due to small size.

Anthers:

*Shape*.—Ovate.

*Length*.—Average 0.2 mm.

*Width*.—Average 0.15 mm.

*Color*.—Near RHS Brown 200A to 200B.

*Pollen*.—Amount: Moderate. Color: Near RHS Greyed-Yellow 160C to 160D.

*Pistil*.—Number: Average 1 per flower. Length: Average 0.2 mm.

*Stigma*.—Shape: Flattened, circular. Length: Average 0.1 mm. Diameter: Average 0.1 mm. Color: Near RHS Grey-Brown N199A. Style: Sessile. Ovary Color: Near RHS Yellow-Green 144B.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12.

What is claimed is:

1. A new and distinct cultivar of *Peperomia* plant named 'EC-PEPE-2104' as herein illustrated and described.

* * * * *